US 8,314,228 B2

(12) United States Patent
Kilian et al.

(10) Patent No.: US 8,314,228 B2
(45) Date of Patent: Nov. 20, 2012

(54) BIDIRECTIONAL PROMOTERS IN NANNOCHLOROPSIS

(75) Inventors: Oliver Kilian, Alameda, CA (US); Bertrand Vick, Emeryville, CA (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 12/706,683

(22) Filed: Feb. 16, 2010

(65) Prior Publication Data

US 2010/0210832 A1 Aug. 19, 2010

Related U.S. Application Data

(60) Provisional application No. 61/207,564, filed on Feb. 13, 2009.

(51) Int. Cl.
*C07H 21/04* (2006.01)
*C12N 15/83* (2006.01)
*C12N 5/14* (2006.01)

(52) U.S. Cl. ............... 536/24.5; 435/320.1; 435/419

(58) Field of Classification Search ............ None
See application file for complete search history.

(56) References Cited

U.S. PATENT DOCUMENTS

| 3,962,466 A | 6/1976 | Nakabayashi |
| 5,105,085 A | 4/1992 | McGuire et al. |
| 5,661,017 A | 8/1997 | Dunahay et al. |
| 5,668,298 A | 9/1997 | Waldron et al. |
| 5,823,781 A | 10/1998 | Hitchcock et al. |
| 6,027,900 A | 2/2000 | Allnutt et al. |
| 6,143,562 A | 11/2000 | Trulson et al. |
| 6,297,054 B1 | 10/2001 | Maliga et al. |
| 6,831,040 B1 | 12/2004 | Unkefer et al. |
| 6,871,195 B2 | 3/2005 | Ryan et al. |
| 7,244,609 B2 | 7/2007 | Drocourt et al. |
| 7,410,637 B2 | 8/2008 | Sayre et al. |
| 7,547,551 B2 | 6/2009 | Schuler et al. |
| 2003/0140021 A1 | 7/2003 | Ryan et al. |
| 2003/0143743 A1 | 7/2003 | Schuler et al. |
| 2003/0199490 A1 | 10/2003 | Antoni-Zimmermann et al. |
| 2003/0211089 A1 | 11/2003 | Sayre et al. |
| 2004/0161364 A1 | 8/2004 | Carlson |
| 2004/0262219 A1 | 12/2004 | Jensen |
| 2005/0064577 A1 | 3/2005 | Berzin |
| 2005/0095569 A1 | 5/2005 | Franklin |
| 2005/0124010 A1 | 6/2005 | Short et al. |
| 2005/0181345 A1 | 8/2005 | Bradbury et al. |
| 2005/0260553 A1 | 11/2005 | Berzin |
| 2006/0031087 A1 | 2/2006 | Fox et al. |
| 2006/0044259 A1 | 3/2006 | Hotelling et al. |
| 2006/0101535 A1 | 5/2006 | Forster et al. |
| 2006/0155558 A1 | 7/2006 | Corpening |
| 2006/0166243 A1 | 7/2006 | Su et al. |
| 2006/0192690 A1 | 8/2006 | Philipp |
| 2007/0178451 A1 | 8/2007 | Deng et al. |
| 2008/0118964 A1 | 5/2008 | Huntley et al. |
| 2008/0120749 A1 | 5/2008 | Melis et al. |
| 2008/0160488 A1 | 7/2008 | Younkes et al. |
| 2008/0160591 A1 | 7/2008 | Willson et al. |
| 2008/0194029 A1 | 8/2008 | Hegemann et al. |
| 2008/0293132 A1 | 11/2008 | Goldman et al. |
| 2009/0029445 A1 | 1/2009 | Eckelberry et al. |
| 2009/0061928 A1 | 3/2009 | Lee et al. |
| 2009/0148931 A1 | 6/2009 | Wilkerson et al. |
| 2009/0317857 A1 | 12/2009 | Vick et al. |
| 2009/0317878 A1 | 12/2009 | Champagne et al. |
| 2009/0317904 A1 | 12/2009 | Vick et al. |
| 2009/0319338 A1 | 12/2009 | Parks et al. |
| 2009/0325270 A1 | 12/2009 | Vick et al. |
| 2010/0100520 A1 | 4/2010 | Dargue et al. |
| 2010/0198659 A1 | 8/2010 | Meltzer et al. |
| 2010/0323387 A1 | 12/2010 | Bailey et al. |
| 2010/0330643 A1 | 12/2010 | Kilian et al. |
| 2011/0059495 A1 | 3/2011 | Bailey et al. |
| 2011/0091977 A1 | 4/2011 | Kilian et al. |

FOREIGN PATENT DOCUMENTS

| WO | WO2004/106238 A2 | 12/2001 |
| WO | WO/2008/060571 A2 | 5/2008 |
| WO | WO/2008/060571 A3 | 11/2008 |
| WO | WO/2008/060571 | 2/2009 |
| WO | WO2009/149470 A1 | 12/2009 |
| WO | WO2010/011335 A1 | 1/2010 |
| WO | WO2011/011463 A2 | 1/2011 |
| WO | WO2011/049995 A1 | 4/2011 |

OTHER PUBLICATIONS

AG610981, Mus musculus molossinus DNA. Abe et al. 2004.*
CO268749, *Drosophila melanogaster* cDNA clone EK092604. Kopczynski et al. 2004.*
Prein et al., "A Novel Strategy for Constructing N-terminal Chromosomal Fusions to Green Fluorescent Protein in the Yeast *Saccharomyces cerevisiae*," FEBS Letters 485 (2000) 29-34.
Wendland et al., "PCR-Based Methods Facilitate Targeted Gene Manipulations and Cloning Procedures," Curr. Gen. (2003) 44: 115-123.
Kindle, et al., "Stable Nuclear Transformation of Chlamydomonas Using the Chlamydomonas Gene for Nitrate Reductase," The Journal of Cell Biology 109(6, part 1): 2589-2601.
Endo et al., "Inactivation of Blasticidin S by *Bacillus cereus* II. Isolation and Characterization of A Plasmid, pBSR 8, From *Bacillus cereus*," The Journal of Antibiotics 41(2): 271-273 (1988).
Schiedlmeier et al., "Nuclearn Transformation of Volvox Carteri," Proceedings of the National Academy of Sciences USA 91(11): 5080-5084 (May 1994).
Hallmann et al., "Genetic Engineering of the Multicellular Green Alga Volvox: A Modified and Multiplied Bacterial Antibiotic Resistance Gene as a Dominant Selectable Marker," The Plant Journal 17(1): 99-109 (Jan. 1999).

(Continued)

*Primary Examiner* — Celine Qian
(74) *Attorney, Agent, or Firm* — Carr & Ferrell LLP

(57) ABSTRACT

Exemplary embodiments provided herein include novel promoters isolated from the microalgae, *Nannochloropsis*. These promoters drive gene expression in a bidirectional manner, and are especially useful for the genetic manipulation of *Nannochloropsis* and other organisms. The inventors herein successfully used these promoters (in both parallel and antiparallel orientations with respect to a Sh ble gene cassette) to impart zeocine-resistance to *Nannochloropsis*.

7 Claims, 3 Drawing Sheets

OTHER PUBLICATIONS

Molnar et al. Highly specific gene silencing by artificial microRNAs in the unicellular alga *Chlamydomonas reinhardtii*. Plant Jour. ePub Jan. 17, 2009 vol. 58 No. 1 pp. 157-164. Especially abstract.

Chen et al. Conditional Production of a Functional Fish Growth Hormonal in the Transgenic Line of *Nannochloropsis oculata* (*Eustigmatophyceae*). J. Phycol. Jun. 2008 vol. 44 No. 3 pp. 768-776. Especially abstract.

Nelson et al. Targeted Disruption of the NIT8 Gene in *Chlamydomonas reinhardtii*. Mol. Cell Bio. Oct. 1995, vol. 15, No. 10, pp. 5762-5769. Especially abstract and p. 5763 left col. para 2.

Csogor et al. "Light distribution in a novel photobioreactor—modeling for optimization" Journal of Applied Phycology, vol. 13, p. 325-333, May 2001, Entire document, especially: abstract; p. 110, col. 1-2 [online]. Retrieved p77j66g3j2133522/fulltext.pdf (NPL 0012).

Genbank Accession No. U71602 (Nannochloropsis sp. Violaxnthin/chlorophyll a binding preotein precursor (NANVCP) mRNA), 1996 (NPL 0017).

Janssen, M. "Photosynthetic efficiency of *Dunaliella tertiolecta* under short light/dark cycles" Enzyme and Microbial Technology, 29, 2001, pp. 298-305 (NPL 0022).

Janssen et al. "Enclosed outdoor photobioreactors: light regime, photosynthetic efficiency, scale-up, and future prospects" Biotechnology and Bioengineering, vol. 81, No. 2, p. 193-210, Jan. 20, 2003, Entire document, especially: Fig 4, p. 198 [online]. Retrieved from the Internet on [Oct. 5, 2010]. Retrieved from: <URL: http://onlinelibrary.wiley.com/doi/10.1002bit.10468/pdf (NPL 0023).

Roessler et al. (Generic Engineering Approaches for Enhanced Production of Biodiesel Fuel from Microalgae, ACS Symposium Series; American Chemical Society, 1994; p. 255-270). (NPL 0036).

Saenz, M.E. "Effects of Technical Grade and a Commercial Formulation of Glyphosate on Algal Population Growth" Bulletin of Environmental Contamination Toxicology, 1997, pp. 638-644 (NPL 0037).

Shi et al. Analysis of expressed sequence tags from the marine microalga *Nannochloropsis oculata* (*Eustigmatophyceae*) J Phycol v 44, p. 99-102 (2008). (NPL 0040).

Strzepek et al., "Photosynthetic architecture differs in coastal and oceanic diatoms" Nature vol. 431, p. 689-692, Oct. 7, 2004. Entire document, especially: abstract, p. 689, col. 2; p. 691, Table 1 [online] Retrieved from the Internet on [Oct. 5, 2010]. Retrieved from: URL:http://www.nature.com/nature/journal/v431/n7009/pdf/nature02954.pdf. (NPL 0043).

Sukenik et al (Journal of Psychology. Jun. 2000; 36(3): 563-570) (NPL 0044).

Thiel et al. Transformation of a Filamentous Cyanobacterium by Electroporation. Journal of Bacteriology. Oct. 1989, vol. 171, No. 10, pp. 5743-5746, especially p. 5743, abstract, p. 5744, left column, first paragraph, Fig 1. (NPL 0045).

Zittelli et al. "Mass cultivation of *Nannochloropsis sp.* In annular reactors" Journal of Applied Phycology vol. 15, p. 107-113, Mar. 2003. Entire document, especially: abstract; p. 110, col. 1-2 [online]. Retrieved from the Internet on [Oct. 5, 2010]. Retrieved from: <URL: http://www.springerlink.com/content/v77772k1mp081775/fulltext.pdf (NPL 0047).

U.S. Appl. No. 12/581,812, filed Oct. 19, 2009, Oliver Kilian, Homologous Recombination in an Algal Nuclear Genome.

U.S. Appl. No. 13/011,809, filed Jan. 21, 2011, Oliver Kilian, Genes for Enhanced Lipid Metabolism for Accumulation of Lipids.

U.S. Appl. No. 12/840,269, filed Jul. 20, 2010, Shaun Bailey, Manipulation of an Alternative Respiratory Pathway in Photo-Autotrophs.

\* cited by examiner

```
>C1 (NT6)    pJET FOR Insert, then pJET rev region
pJET FOR >> CAT ACTTAAGAAGTGGTGGTTGGTGGTGC (P168)
TGCTGCTGTAGAGGATATGGCATGGGGGTGGGACGAGGGGATGTAAGTGTTGCGATGTTTTGAGGGGTTTCGTCGGGTATGTGCGAGTCGTGTGAAGATGTG
GAGCACGTGTGGAAAAGGGCAAGAGAACTGGGCAGAGAACGTATCTAGGTTTGAAAGCACTCTTCATACTTGATCGTTGATACGCAACTCAAGGGAAAGGTCTCTGA
AAGAACAAGAGCGAGAGCCCAGGCTCCTAGAAGGAAGAGAGCAAGGGAGGTCTGTCCATGTCAATCAGGTAAAGCACAAAGAGCGAAGTACAAGTATCAGCTC
TAGCAACTTGGTCAACTAGCTGGGTTTCTTGTGACAGGGAAAGACTGTTGAAGATAGATCAGGGGGCACTTATGGCTCAAGAGGGTTGAGCTGAGCCTGTTCCC
TCGCTCCGCTTTGTCCGACGACAGAAGGCTTTGCGGGTCTGCCCTGGGATCCTACTGCAAGGTTGAGCGCGTTGAGCAGACCCATGGGAGGTCGTTGAGGCTTTC
GGCACTAAGACAAGATAGGCAAGATGCCCCAATGTCCTGTTACCAACTGGGGGTTGTGGAAGCACGCGTCGGAGCCTCAAGGGCTCGTTGATAAGGGGATGAAATCGTCC
CGGCGAGCAAATCCTGGTTGACCTGCAGGATCGTTGAAAAGCAGGAGGCACGTTCGGCGCGAGCCGGTCGCGCGCGAGCCGGTTCCTGCCATGGAC
GTTTGGTTGTTTGACTACTGCTTGACTCTTGTCATATGTTTATTTGGTGCATGTGTTTCTCCTTCTGTCTGTGCCACTGCACCCCAGCGGTTCTGCCCATGGAC
AGGACACCATCGCACCTGACCTCCCTGTCCTCCTCCAAGCCCCATCTCTTCGGCCGTGGGACAATGAaGGGATGGCAGGGAAGATCTGCTTGGTATCTCACTCTA
AGCACAATCAAGACAGTCACAGACACGCAGCAGGCCCTCCACACAGCCTCATTTAtCACATGCCACCTTCGCCACCTTCGACTCACGCTCCGCCCTTTCCC
TCCCCAAACACTCCACGATAGTCAACTTCCACCACTCTCTCAAGT ATGGCCAAGTTGACCAGTTGCCGTTCCGGTGCCGTTCACCGCGCGGACGTCGGCCGGACGACCGGCTCGGGTTCTCCGGACTTCGTGGAGG
ACGACTTCGCCGGGTGTGGTCCGGGACGACGTGTTCATCAGCCGCGGTGTCGGAACCTGGTGCCGGTCCAGGACCAACACCCCTGGCCCTGGGTGTGGGTGCGCGGCCT
GGACGAGCTGTACGCCGAGTGGTCGGAGGTCGTGTCCACGAACTTCCGGGCGCCTGACCGGCCATGCGAGCGAGATCGGGCAGCCGTGGGGCGGGAGTT
CGCCCTGCGCGACCCGGCCGGCAACTGCCTCGTGCACTTCGTGGGCCAGGAGCAGGACTAA GCTTCTGTGGAAGAGCCAGTAGTAGCAGCAGCAGCAGCCGCAGCACTCAGTGTTGGCGCGAGAGATTGTCCATCCCTCTTAACCTACCGGAAG
AGAAATAAGGCCTTCTCCCGTGGTTCTCTTTTGTCACCCTTATTTACATAAAATTCTTGTTATAGTGAGAGGAAGGTAGAGAGGGGAAAACAACGAACG
GTCATTTTCTTTCTTTCCCTGGTTCTTCTTTTGTCACCCTATTTTACATAAAATTCTTTGTTATAGTGAGAGGAAGGTAGAGAGGGGAAAACAACGAACG
CAAGCGTGTGAAAGGAGGCGAGTAGAAGAGAAGAAACATCTGTTGAGCATTGAGAGTGGAGCCGGGAGAAGGCTTGTGTTTGTTCTTGAAAAAGTTGTTAA
ATCACGAATCCGTTAGTTCTCATGTGTACCTCTTCACTACTGTGATGGAGAAAACAAAAGTGTGAGGATTAATTGAAGAAAAGAAGAGTTCGACACGTCAAACC
GCCCAAAGACGTCACAAAGAGAACTTGATCTCTTGCCGTGTTGCCGTTGCCGTCGCGTTTTCTGCCACCCGTGGCACACGAGATGGACAAGATCAG
(P119) << pJET REV
```

FIG. 1A

>C2 (NT7) pJET for – Insert – pJet rev
ACTTGAGAGAGTGGTGGAGTTGACT *** ( >> P 169)

ATCGTGTGGAGTGTTTGGGGAGGAAAGGCGGAGCGGAGTGGGCGAAGTGGGCGAAGTGGGCGAAGTGGCAATGCGAGGTGGGCGAAGTGGGCGAAGTGTATAAATGGCTGTGTGGTGAGGCCTTCGT
GCGTGTCTGTGACTGTCTTGATTGTGTGCTTAGAGTGAGATACCAAAGCAAGATCTTCCCATCCCTCATTGTCCCACGGGCCGAAGAgATGGGGGGCTTGA
CGAGAGGACAGGGATGCAGGTGCGATGCCAGTCGGTCCTGTCTGTCCATGGGGCAGGAGAACCGCTGGGGTGCAGTGGCACAGAAGACAGAAGGAGAAACACATGCACCAAA
TAAACATATGACAAAGAGTCAAGCAGTAGTCAAAACAACCAAAACGTAAGCAACAAGATGGCACGCTCTGCAACAGACCGGCTCGCCGAACGT
GCCTCCTGCTTTCAACGATCCTGCGAGGTCAACCAGAGTTTGCTCGCCGGGACGATTTCATCCCCTTATCAACGAGCCCTTGAGGCTCCAGGCGTCTTCCACACC
CCAGTTGGTAACAGGACATTGGGGCATCTGCGAGGTCATCTGCCTCATCTGTCTTAGTGCCGACAAAGCCTCAGTCACCCTCTGATACCTGTCAACCCTCAACCTTGCAGTAAGG
ATCCCGAGGGCAAGACCGCAAAGCTTTCCTGTCACAAGAAAACCAGCTAGTTGACCAAGTTGCTAGAGACCTTTCCCTTGAGTGCGTATCCAGCGATCAAGTATGAAGAGTG
GACAGACCTCCCCTTGCTCTTCCTTCTAGGAGCTTCTGCCCAGTTCTCTTGCCCTTTCCACACGTGCTCACATCTTCACGACTCGCACCATACCGACGAAACCCTCAAAACATCGCA
CTTTCAAACCTAGATACGTTCTGCCCAGTTCTCTTGCCCTTTCCACACGTGCTCACATCTTCACGACTCGCACCATACCGACGAAACCCTCAAAACATCGCA
ACACTTACATCCCGCTCGTGTCCCACCCCGATGCCATATCCTACACAGCAGCACCACCACCACCACTTCTTAAGT

↑
110

ATGGCCAAGTTGACCAGTGCCGTTCCGGTGCTCACCGCGCGACGTCGAGTTCTGGACCAGCGGTCGAGTTCTGGACGACCGGCTCGGGTTCTCCCGGGACTTCG
TGGAGGACGACTTCGCCGGTGCCGGGTGTGGGTCCGGGACGACGTGACCCTGTTCATCAGCGCCGTGCCAGGTGGTGCCGGACAACACCCTGGCCTGGGTGT
GGGTGCCGGGCCTGGACGAGCTGTACGCCGAGTGGTCCACGAACTTCCGGGACGCCTCCGGGCCGGGCCTGACCGAGATCGGCGAG
CAGCCGTGGGGCGGGAGTTCGCCCTGCGCCGACCGGGCCAACTGCTCGTGCACTTCGTGGCCGAGGAGCAGGACTAA

↑
120

GCTTCTGTGGAAGAGCCAGTGGTAGTAGCAGTAGCAGCAGCCGCAGCACTCAGTGTTGGGCGCAGAGATTGTCCATCCCTTCTTAACCTAC
CGGAAGAGAAATAAGGCCTTCTCCCGTAGCGTCTGTTTGTTGTCGATTGCTTGATATGAGAGTGTTGAATTCCTGCATCATGTTTCTCTGTAG
TCCTTCCTACCCCGTCATTTCTTTCTCCCGGTCTTCTTGTCACCCTATTTACATAAAATTTCTTGTTTATAGTGAGAGGAAGGTAGAGAGGG
GAAAACAAGAACAACGAACGCAAGCGTGAAAGGAGGGCGAGTAGAAGAGAAACAGATCTGTTGAGCATTGAGAGTTGGAGCCGGGGAAAGGCTT
GTGTGTTGTCTTGAAAAAGTTGTTAAATCACGAATCCGTAGTTCTCATGTGTACCTCTTCACTACATGTGATGGAGAAAACAAAAGTGTGAGGATTA
ATTGAAGAAAAAAGAAGAGTTCGACACGTCAAACCGCCCAAAGAGACGTCACAAAGAGAACTTGATTCTCTTTGCCGTTGTCTTTGATCCTGTCTTTTCCCCAGCTT
TTCTTGCCACCCGT GGCACACGAGATGGACAAGATCAG (P119)  <<_pJET REV

BIDIRECTIONAL PROMOTERS IN *NANNOCHLOROPSIS*

CROSS-REFERENCE TO RELATED APPLICATIONS

This application claims the benefit and priority of U.S. Provisional Patent Application Ser. No. 61/207,564 filed on Feb. 13, 2009, titled "Bidirectional Promoter in *Nannochloropsis*," which is incorporated by reference herein.

This application is related to U.S. Non-Provisional patent application Ser. No. 12/480,635 filed on Jun. 8, 2009, titled "VCP-Based Vectors for Algal Cell Transformation," which in turn claims the benefit and priority of U.S. Provisional Patent Application Ser. No. 61/059,672 filed on Jun. 6, 2008, titled "VCP-Based Vector For *Nannochloropsis* Transformation," the disclosures of both which are incorporated by reference herein.

REFERENCE TO SEQUENCE LISTINGS

The present application is filed with sequence listing(s) attached hereto and incorporated by reference.

FIELD OF THE INVENTION

This invention relates to molecular biology, and more specifically to the transformation of algal cells and the expression of exogenous deoxyribonucleic acid (DNA).

SUMMARY OF THE INVENTION

Exemplary embodiments provided herein include novel promoters isolated from the microalgae, *Nannochloropsis*. These promoters drive gene expression in a bidirectional manner, and are especially useful for the genetic manipulation of *Nannochloropsis* and other organisms. The inventors herein successfully used these promoters (in both parallel and antiparallel orientations with respect to a Sh ble gene cassette) to impart zeocine-resistance to *Nannochloropsis*.

BRIEF DESCRIPTION OF THE DRAWINGS

FIG. 1A shows exemplary transformation construct NT6.
FIG. 1B shows exemplary transformation construct NT7.

DETAILED DESCRIPTION OF THE INVENTION

Figure 2:
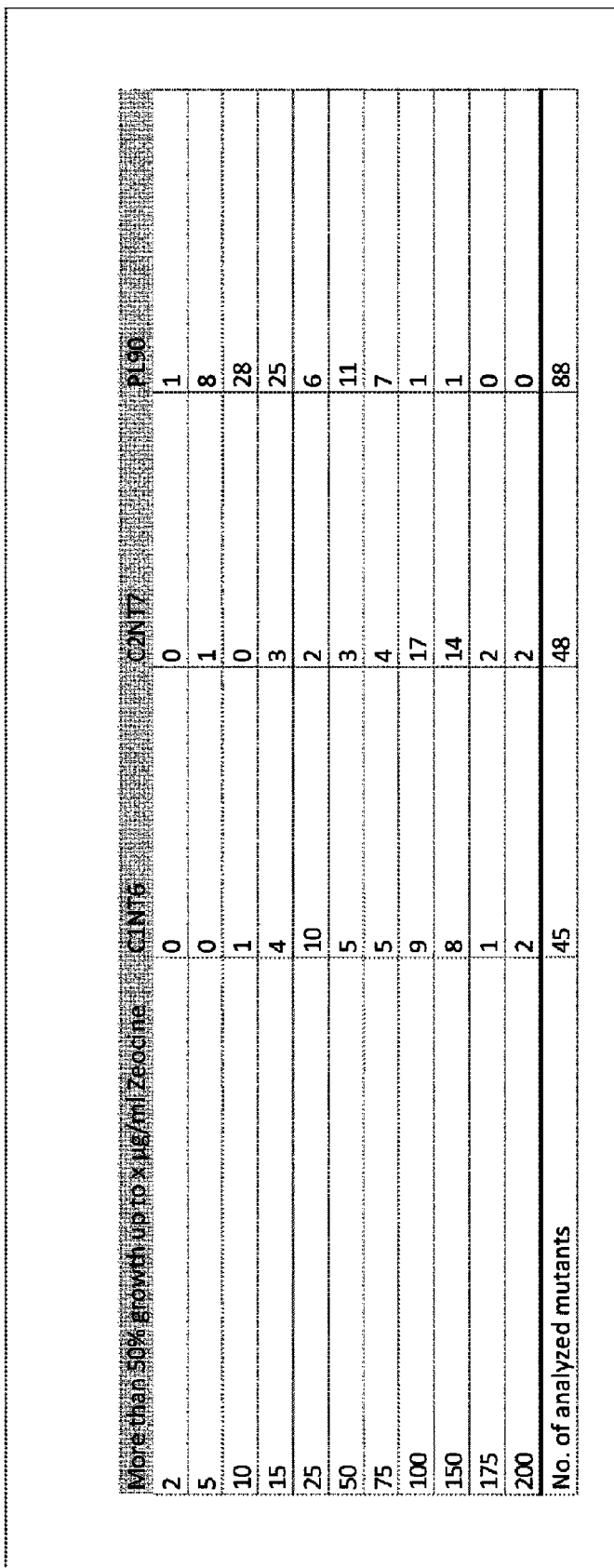
FIG. 2 shows a table reflecting the exemplary results of a growth assay used to analyze the transformants that resulted from the three transformation constructs, NT6, NT7, and PL90.

Exemplary embodiments provided herein include novel promoters isolated from the microalgae, *Nannochloropsis*. These promoters drive gene expression in a bidirectional manner, and are especially useful for the genetic manipulation of *Nannochloropsis* and other organisms. The inventors herein successfully used these promoters (in both parallel and antiparallel orientations with respect to a Sh ble gene cassette) to impart zeocine-resistance to *Nannochloropsis*.

FIGS. 1A-1B show two exemplary transformation constructs, transformation construct NT6 (FIG. 1A) and transformation construct NT7 (FIG. 1B). Transformation construct NT6 as shown in FIG. 1A includes a bidirectional promoter sequence 110 (SEQ. ID. NO. 1), a Sh ble gene cassette sequence 120, and a 3' untranslated region sequence (UTR) 130. Transformation construct NT7 as shown in FIG. 1B includes a bidirectional promoter sequence 110 (SEQ. ID. NO. 2), a Sh ble gene cassette sequence 120, and a 3' untranslated region sequence (UTR) 130.

When analyzing a *Nannochloropsis* genomic sequence, the inventors found two divergently transcribed Vcp genes orientated back to back (i.e. transcription must have been initiated from the nucleotide sequence separating both genes) separated by several hundred nucleotides. The inventors believed that this nucleotide sequence that separated the divergently transcribed Vcp genes included the requisite regulatory elements to drive expression of both divergently transcribed Vcp genes.

The inventors created transformation constructs NT6 and NT7 to confirm they had discovered a bidirectional promoter in the *Nannochloropsis* genome. The bidirectional promoter was amplified from the *Nannochloropsis* genome using Polymerase Chain Reaction (PCR) and other standard techniques. A *Nannochloropsis* transformation construct (or vector) was constructed using a pJet vector as the backbone. The bidirectional promoter was cloned in both a parallel (NT6) and an anti-parallel (NT7) fashion relative to a standard zeocine-resistance (Sh ble) cassette. A Vcp 3'-UTR was placed immediately downstream of the zeocine-resistance (Sh ble) cassette in both constructs.

The NT6 and NT7 transformation constructs were cut out via restriction enzyme digestion and the transformation construct purified after DNA gel electrophoreses. A PL90 transformation construct, as described in U.S. Non-Provisional patent application Ser. No. 12/480,635 filed on Jun. 8, 2009, titled "VCP-Based Vectors for Algal Cell Transformation," that included another Vcp-promoter was linearized to be used as a comparison to the NT6 and NT7 transformation constructs. All three transformation constructs in equimolar amounts were used to transform *Nannochloropsis* cells, which were then allowed to incubate at room temperature under ~85 µE light on solid selective media (with a zeocine concentration of 2 micrograms per milliliter) for several weeks until visible colonies were formed.

FIG. 2 shows a table reflecting the exemplary results of a growth assay used to analyze the transformants that resulted from the three transformation constructs, NT6 (FIG. 1A), NT7 (FIG. 1B), and PL90. The inventors found that the bidirectional promoter sequence 110 (FIGS. 1A-1B) in both orientations (i.e. parallel and anti-parallel) within each transformation construct (i.e. NT6 and NT7) drove much higher levels of gene expression than the Vcp-promoter used in the PL90 transformation construct.

Referring again to FIG. 2, the growth assay utilized zeocine, an antibiotic that kills most aerobic cells by binding and cleaving the DNA in the aerobic cells. The Sh ble gene product produced by the Sh ble gene cassette sequence 120 (FIGS. 1A-1B) prevents toxicity by binding to zeocine and inactivating it. Accordingly, a higher level of Sh ble-transgene expression in an algal cell will lead to a greater ability for the algal cell to survive in higher zeocine concentrations.

Zeocine was utilized in a kill-curve as follows:

1. 1 mL aliquots of F2 media were added to wells in a 24-well plate.
2. Zeocine was added to the wells with F2 media to achieve final concentrations of zeocine as listed in the left-hand column of the FIG. 2 table (i.e. the final concentrations of zeocine ranged from 0 ug/ml to 200 ug/ml).
3. Colonies were randomly picked from agar plates containing the NT6, NT7, and PL90 transformants (the number of transformants tested for each transformation construct is given as the final line-item in the FIG. 2 table).
4. Each colony was resuspended in 30 uL of N2 media.

5. 2 uL of each colony-resuspension was added to the wells containing the increasing amounts of zeocine (wells without zeocine were included as controls, but are not shown in the FIG. 2 table).

6. The 24-well plates were allowed to incubate under 85 uE light for 1 week.

7. Optical density measurements (at 750 nm) for each well were obtained with a spectrophotometer.

8. For each transformant, the highest zeocine concentration was determined required to enable at least 50% growth of the cell line as compared to the no-zeocine controls.

The exemplary data reflected in the FIG. 2 table shows the number of colonies that had at least 50% survival up to the specified zeocine concentration. The data in the FIG. 2 table shows that the NT6 and NT7 transformation constructs withstood higher levels of zeocine than did the PL90 transformation construct. Because the promoter was the only variable between the NT6/NT7 and PL90 transformation constructs, it followed that the increased survival rate of the NT6/NT7 transformation constructs was due to the bidirectional promoter, which is apparently stronger than the Vcp-promoter used in the PL90 transformation construct. It should be noted that wild-type Nannochloropsis will generally not survive zeocine concentrations of 2 micrograms per milliliter and higher.

The various exemplary bidirectional promoters provided herein have been used to drive expression of genes introduced to Nannochloropsis via transformation. They also may be used to perform activation-tagging random insertional mutagenesis experiments. To achieve certain phenotypes through genetic manipulation, up-regulation of the expression of certain genes (as opposed to the down-regulation or the knocking out of certain genes) may be required. Forward genetics may be performed with the bidirectional promoter in a highly efficiently manner because the promoter can activate genes in both directions. A typical activation tagging experiment, to achieve higher oil production, could be performed as follows: A transformation construct comprising the bidirectional promoter as depicted in FIG. 1A or 1B, a selection gene (e.g. the Sh ble gene), and an 5' UTR, is isolated via PCR or restriction digest of the plasmid containing the bidirectional promoter would be introduced into Nannochloropsis via previously-described methods. The bidirectional promoter would each be inserted into the Nannochloropsis genome in random locations when individual transformants are analyzed, and at some frequency, it would insert upstream of the genes involved in, e.g., lipid biosynthesis. Compared to the promoters of genes involved with lipid biosynthesis, the Vcp promoters, being strong promoters, would likely drive higher expression of the gene(s). An assay, such as the Nile Red assay, could be performed to identify transformants that produce more lipids.

The various exemplary bidirectional promoter sequences provided herein may be used to perform RNA-interference (RNAi). RNAi is based on the presence of dsRNA, either introduced exogenously or produced within a cell itself. The bidirectional promoter provides for a facile system to perform RNAi, as the gene of interest can be expressed in parallel and anti-parallel fashions, thus making reverse complements of one another (dsRNA).

What is claimed is:

1. A bidirectional promoter for a transformation construct for algal cell transformation, the bidirectional promoter comprising the nucleotide sequence of SEQ. ID. NO. 1.

2. The bidirectional promoter of claim 1, wherein the algal cell is of algal genus *Nannochloropsis*.

3. The bidirectional promoter of claim 1, wherein the bidirectional promoter promotes transcription of a first nucleotide sequence adjacent to a first side of the bidirectional promoter in a 3' direction and the bidirectional promotes transcription of a second nucleotide sequence adjacent to a second side of the bidirectional promoter in a 5' direction.

4. The bidirectional promoter of claim 3, wherein the bidirectional promoter promotes transcription of the first and the second nucleotide sequences at a same time.

5. The bidirectional promoter of claim 3, wherein the first nucleotide sequence includes a selection marker gene.

6. The bidirectional promoter of claim 3, wherein the second nucleotide sequence includes a selection marker gene.

7. The bidirectional promoter of claim 5 or claim 6, wherein the selection marker gene is a Sh Ble gene.

* * * * *

SEQUENCE LISTING

<160> NUMBER OF SEQ ID NOS: 2

<210> SEQ ID NO 1
<211> LENGTH: 1132
<212> TYPE: DNA
<213> ORGANISM: Nannochloropsis sp. W2J3B

<400> SEQUENCE: 1

```
tgctgctgta gaggatatgg catcgggggt gggacacgag cgggatgtaa gtgttgcgat      60
gttttgaggg gtttcgtcgg gtatggtgcg agtcgtgtga agatgtggag cacgtgtgga     120
aaagggcaag agaactgggc agaacgtatc taggtttgaa agcactcttc atacttgatc     180
gctggatacg caactcaagg gaaaggtctc tcgaaagaac aagagcgaga gcccaggctc     240
ctagaaggaa gagcaagggg aggtctgtcc atgtccaatc aggtaaagca cacaaagagc     300
gaagtacaag gtatcagctc tagcaacttg gtcaactagc tgggttttct tgtgacaggg     360
aaagactgtt gaagatagat caggggcac ttatgggctc tcaagagggt tgagctgagc      420
ctgttccctc gctccgcttt gtccgacgac agaaggcttt gcgggtcttg ccctcgggga     480
tccttactgc aaggttgagg cgttgagcag accccatggg aggtcgttga ggctttcggc     540
actaagacaa gataggcaag atgccccaat gtcctgttac caactggggt gtggaagcac     600
gcctggagcc tcaagggctc gttgataagg ggatgaaatc gtcccggcga gcaaatcctg     660
gttgacctcg caggatcgtt gaaaagcagg aggcacgttc ggcgcgagcc ggtctgttgc     720
agacgcgtgc catcttgttc cgtcttgctt acgttttggt tgttttgact actgcttgac     780
tctttgtcat atgtttattt ggtgcatgtg ttttctcctt ctgtcttctg tgccactgca     840
ccccagcggt tcctgcccca tggacaggac cgcatcgcac ctgcatccct gtcctctcgt     900
```

-continued

```
caagcccccc atctcttcgg cccgtgggac aatgaaggga tggcagggaa gatcttgctt      960
tggtatctca ctctaagcac acaatcaaga cagtcacaga cacgcagcga aggcctccac     1020
cacacagcca tttatcacat gcccacttcg cccacctcgc attgcactca cgctccgccc     1080
tttccctccc caaacactcc acacgatagt caactccacc actctctcaa gt             1132
```

<210> SEQ ID NO 2
<211> LENGTH: 1132
<212> TYPE: DNA
<213> ORGANISM: Nannochloropsis

<400> SEQUENCE: 2

```
atcgtgtgga gtgtttgggg agggaaaggg cggagcgtga gtgcaatgcg aggtgggcga       60
agtgggcatg tgataaatgg ctgtgtggtg gaggccttcg ctgcgtgtct gtgactgtct      120
tgattgtgtg cttagagtga gataccaaag caagatcttc cctgccatcc cttcattgtc      180
ccacgggccg aagagatggg gggcttgacg agaggacagg gatgcaggtg cgatgcggtc      240
ctgtccatgg ggcaggaacc gctggggtgc agtggcacag aagacagaag gagaaaacac      300
atgcaccaaa taaacatatg acaaagagtc aagcagtagt caaaacaacc aaaacgtaag      360
caagacggaa caagatggca cgcgtctgca acagaccggc tcgcgccgaa cgtgcctcct      420
gcttttcaac gatcctgcga ggtcaaccag gatttgctcg ccgggacgat ttcatcccct      480
tatcaacgag cccttgaggc tccaggcgtg cttccacacc ccagttggta acaggacatt      540
ggggcatctt gcctatcttg tcttagtgcc gaaagcctca acgacctccc atggggtctg      600
ctcaacgcct caaccttgca gtaaggatcc ccgagggcaa gacccgcaaa gccttctgtc      660
gtcggacaaa gcggagcgag ggaacaggct cagctcaacc ctcttgagag cccataagtg      720 cccccctgatc tatcttcaac agtctttccc tgtcacaaga aaacccagct agttgaccaa     780
gttgctagag ctgataccttc gtacttcgct cttttgtgtgc tttacctgat tggacatgga    840
cagacctccc cttgctcttc cttctaggag cctgggctct cgctcttgtt ctttcgagag      900
acctttccct tgagttgcgt atccagcgat caagtatgaa gagtgctttc aaacctagat      960
acgttctgcc cagttctctt gccctttttcc acacgtgctc cacatcttca cacgactcgc    1020
accatacccg acgaaacccc tcaaaacatc gcaacactta catcccgctc gtgtcccacc    1080
cccgatgcca tatcctctac agcagcagca ccaccaccac cacttcttaa gt            1132
```